United States Patent [19]

Naser et al.

[11] Patent Number: 4,921,198

[45] Date of Patent: May 1, 1990

[54] HOLDING MECHANISM FOR A MEASURING CRYOSTAT

[75] Inventors: Georg Naser, Zirndorf; Peter Reichelsdoerfer, Aalen; Siegfried Schneider, Erlangen, all of Fed. Rep. of Germany

[73] Assignee: Siemens Aktiengesellschaft, Berlin and Munich, Fed. Rep. of Germany

[21] Appl. No.: 128,172

[22] Filed: Dec. 3, 1987

[30] Foreign Application Priority Data

Dec. 9, 1986 [DE] Fed. Rep. of Germany ....... 3641945

[51] Int. Cl.⁵ ................................................ A61B 5/05
[52] U.S. Cl. .................................. 248/123.1; 378/198; 414/772; 414/779
[58] Field of Search ............................ D24/7, 17, 29; 128/653 SC; 248/123.1; 378/197, 198; 414/680, 728, 742, 754, 764, 767, 743, 772, 776, 779, 782, 784; 600/13, 14, 15; 901/18

[56] References Cited

U.S. PATENT DOCUMENTS

| | | | |
|---|---|---|---|
| 4,653,083 | 3/1987 | Rossi | 378/197 X |
| 4,716,581 | 12/1987 | Barud | 378/197 X |
| 4,741,015 | 4/1988 | Charrier | 378/197 X |

FOREIGN PATENT DOCUMENTS 391384  3/1924 Fed. Rep. of Germany ...... 378/197
739460 10/1955 United Kingdom .

OTHER PUBLICATIONS

D. Crum, "The Design and Use of Dewars for Biomagnetic Measurements" *Biomagnetism: Applications & Theory*, Proceedings of the Fifth World Conference on Biomagnetism, Vancouver, Canada, Aug., 1984, Edited by H. Weinburg, C. Stroink and T. Katila, Pergamon Press, pp. 21-34.

*Primary Examiner*—Robert J. Spar
*Assistant Examiner*—Janice Krizek
*Attorney, Agent, or Firm*—Hill, Van Santen, Steadman & Simpson

[57] ABSTRACT

A holding mechanism for vertically positioning a measuring cryostat relative to a patient includes a pair of spaced, vertically-extending columns, which are preferably connected at their upper ends by a cross member, each of said columns has a box vertically movable along the column. The two boxes are interconnected by a shackle which is mounted at each end for rotation on the boxes, and the shackle includes an arrangement for mounting the cryostat on the shackle which allows pivoting of the cryostat in a plane of the shackle. Thus, the structure allows for both rotating the cryostat around an axis around a point and pivoting in a plane extending perpendicular to the direction of rotation around the same point. In addition, the mechanism enables vertically positioning the point relative to a patient or other object.

16 Claims, 2 Drawing Sheets

HOLDING MECHANISM FOR A MEASURING CRYOSTAT

BACKGROUND OF THE INVENTION

The present invention is directed to a holding mechanism for mounting a measuring cryostat which is used to acquire biomagnetic signals.

Since the measuring cryostat comprises a magnetic measuring coil and the movement of this coil in the micrometer range is undesirable, high demands are made on the stability of a holding mechanism for the cryostat. At the same time, the greatest possible flexibility with respect to the manipulatability and adjustability of the measuring cryostat having the coil should be established.

Included in these demands is an easy height adjustability for different measuring positions given a patient who is either lying or sitting, and also a height adjustment for working with the cryostat, such as when replenishing the liquid helium therein. Also included in these requirements is the simple maneuverability of the measuring cryostat on a spherical surface, whose center lies within either the head or the thorax of the patient being tested or measured. The radius of the spherical surface to be traversed should, therefore, be adjustable insofar as possible. In addition, the measuring coil should be capable of being adjusted relative to the interesting measurement region of the head or thorax of the patient and be also adjustable by rotating the measuring element relative to the cryostat axis.

Another desirable condition, which should also be met, is that the holding mechanism is as free as possible of any mechanical resonance. Finally, the mechanism should also provide access to the patient and to the cryostat for the purpose of maintenance work. In addition, the safety standards for the protection of the patient which is standard in medical technology must be observed and achieved.

A measuring cryostat of the type under consideration in the present invention for the measurement of biomagnetic signals is known. An example is disclosed by an article by D. Crum "The Design and Use of Dewars for Biomagnetic Measurements", *Biomagnetism: Application and Theory*, edited by H. Weinberg et al, Pergamon Press, New York, 1985, pp. 21–34.

SUMMARY OF THE INVENTION

The object of the present invention is to provide a holding mechanism which meets the above-mentioned demands as easily as possible.

This object is inventively achieved in that the holding mechanism comprises two vertical standing columns, a travelling box being displaceably arranged on each of the two columns, a shackle having, at each end, means for rotatably connecting the end to one of the travelling boxes so that the shackle extends between the two columns, said shackle having means for mounting a cryostat for pivotal movement in a shackle plane of the shackle.

A simple height adjustment of the cryostat is therefore achieved as a result of displacement of the travelling boxes on each of the vertically extending columns. The means for rotatably securing the shackle to each of the boxes, as well as the means for pivotably mounting the cryostat in the plane of the shackle, enables the transversal of the measuring cryostat on a spherical surface. The center of the surface can be selected so that it will lie on the inside of a head or of a thorax of a patient who is being examined. When both the vertical columns are directly secured on a structural foundation having a comparably large mass, a high stability, and a freedom from vibrations will be achieved.

Other advantages and developments of the invention will be readily apparent from the following description of the preferred embodiments with reference to the Figures and claims.

DESCRIPTION OF THE PREFERRED EMBODIMENTS

Figure 1:
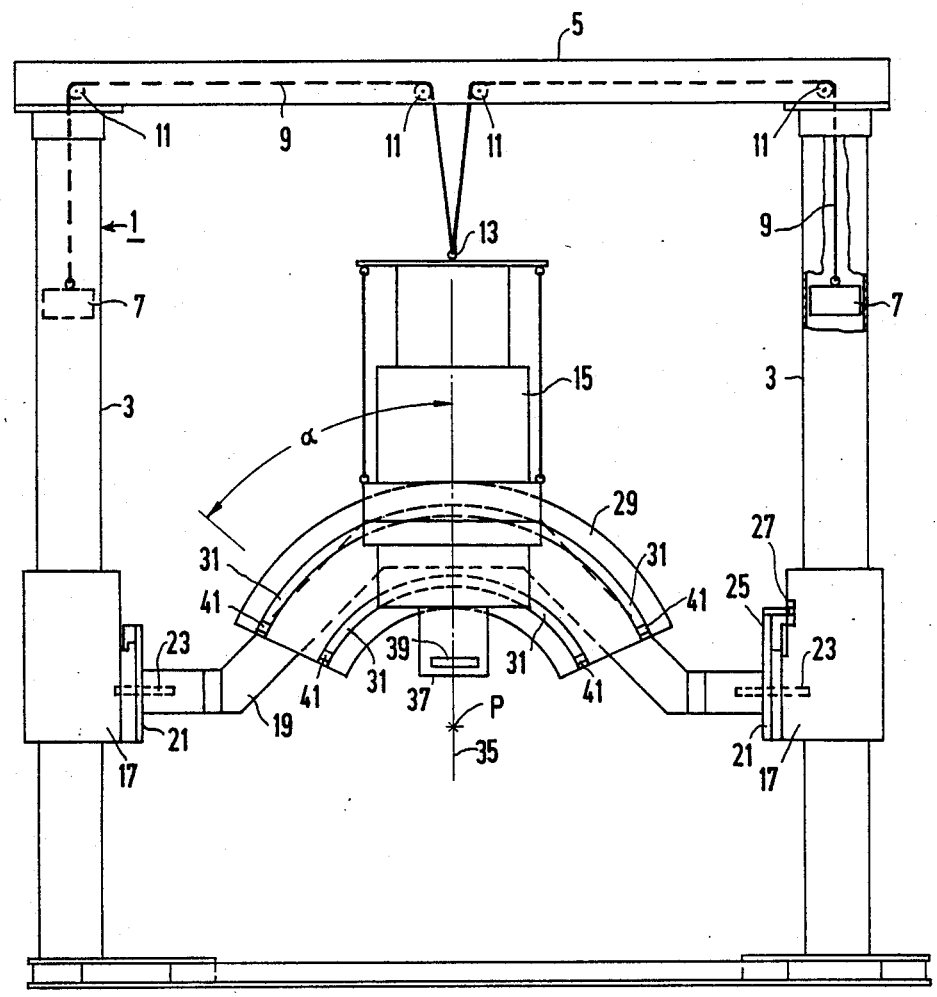
FIG. 1 is a side view of a holding mechanism for measuring cryostat in accordance with the present invention.
Figure 2:
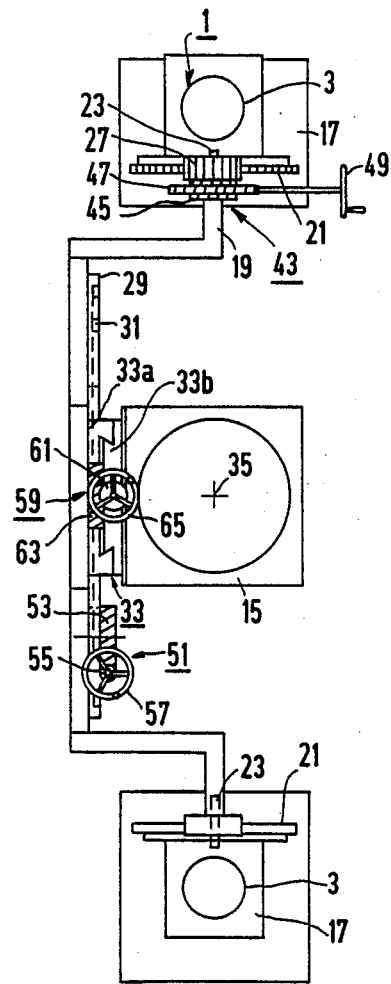
FIG. 2 is a plan view of the holding mechanism of FIG. 1.

The principles of the present invention are particularly useful when incorporated in a holding mechanism, which is generally indicated at 1 in FIGS. 1 and 2. The holding mechanism 1 is formed by two vertically standing columns 3 which are connected to one another on their upper ends via a cross-stay or member 5. The columns 3 are hollow and each column accepts an internally displaceable counterweight 7. Each of the counterweights 7 is connected by a cable 9, which passes over deflection rollers 11 and has the other end connected to an eyelet 13, which is secured to a means for mounting a measuring cryostat 15. While the two cables 9 are illustrated as being connected to the same eyelet, they can be connected individually to different portions of the means for mounting. The measuring cryostat 15 is a known unit in and of itself. It contains a measuring coil, such as 39, which is cooled by liquid helium and serves the purpose of acquiring biomagnetic signals of a patient, which signals are caused, for example, by brain currents.

A travelling box 17 is telescopically received on each of the columns 3 in a height-displaceable fashion. The travelling boxes 17 are connected to one another via a shackle 19. Each end of the shackle 19 has means for forming a rotatable connection to the box 17, which means comprises a circular disk segment 21, which is rotated on a pin 23 secured to the travelling box 17. At least one of the disk segments 21 is provided with a gear rim 25, which meshes with a drive gear 27 to control rotation of the shackle relative to the box 21 about the axis formed by the pin 23. The shackle can, thus, be swivelled or rotated about this axis defined by the pair of pins 23.

A member 29, which is a segment of a circular ring, is attached in the middle of the shackle 19. This circular ring segment 29 is provided with one or, preferably, a plurality of concentric, circular segment-shaped channels 31. The measuring cryostat 15 is pivotably mounted by the means for mounting to the channels 31 via tenon blocks which are secured therein. The angle of pivoting or swivelling relative to a vertical axis is indicated by an angle α. The displacement by the angle α occurs via a spur gear drive. The circular ring segment 29 is aligned to extend parallel to a shackle plane when being pivoted.

The means for mounting the measuring cryostat 15 includes a carriage 33 (FIG. 2), which allows displacement of the cryostat along an axis 35 relative to the circular segment 29. The displacement thereby occurs in a radial direction and is in the direction of the radius of the circular segment 29. The means for mounting the cryostat also includes a plain bearing to allow rotation of the cryostat around the central axis 35.

With the assistance of the above-described counter-weights 7 in combination with the cables 9 and the deflection rollers 11, the overall unit comprising the cryostat, the means for mounting the cryostat on the circular ring segment 29, the shackle and the travelling boxes 17 are displaceable vertically on each of the columns 3. In addition to the mechanical reinforcements, the cross-stay 5 thus also simultaneously serves as a bridge for a weight equalization between the weight of the measuring cryostat on the one hand and the counter-weights 7, which are received in the interior of each of the columns 3. This height adjustment serves the purpose of bringing the application surface 37 of the cryostat 15, which surface 37 is adjacent the measuring coil 39, to lie tightly against either a surface of a patient who may be sitting or against a surface of a patient who may be lying down. Moreover, replenishing liquid helium is facilitated given a complete lowering of the measuring cryostat 15, and this filling is in the upper end of the cryostat. For reasons of patient and apparatus safety, a toothed rack is attached to at least one of the columns 3, and a catch lever, which will prevent an unintentional lowering of the measuring system is engaged in this rack. When adjusting the height of the measuring device, the latch must be intentionally released, and this latch then enqaqes into the next index notch as a result of a spring acting thereon.

The measuring cryostat 15 is displaceable through an angle α along the channels 31. The maximum angle α is about 50° on each side. The channels 31 are provided with stops 41 at each end, and these stops prevent the cryostat 15 from pivoting to such an extent, that it would strike against one of the columns 3. During pivoting, the application face 37 will remain aligned to the same point P, both when pivoted through the angle α as well as when the shackle is rotated relative to the boxes 17. The mechanism is usually adJusted so that the point P is placed in the head or in the thorax of the patient being measured. The distance between the application surface 37 and the point P can be varied with the assistance of the carriage 33 of the mounting means.

It is further apparent from FIG. 2 that a worm gear arrangement 43 is associated with the drive gear 27 at least on one side. The worm gear arrangement 43 comprises a gear wheel 45 having angled teeth, a corresponding worm wheel 47 and a crank disk 49 having a handle. This arrangement enables the cryostat to be adjusted more accurately and also allows the pin 23 to be turned with greater ease. Furthermore the worm gear arrangement is chosen to be self-braking. The measuring cryostat is therefore always firmly positioned, which contributes to the safety of the patient. These same advantages are associated with the worm gear arrangement 51 (comprising gear wheel 53, worm wheel 55 and crank disk 57), which is disposed between the carriage 33 and the circular ring segment 29 and which is used for displacing the cryostat through angle α and arresting it. In FIG. 2 the carriage is subdivided into two parts 33a and 33b. The part 33a is positioned in the channel 31. Part 33b is displaceable relative to part 33a in the radial direction, for example via a dovetail slide. The angle is given by displacing part 33a along the channel 31. This, in turn, causes part 33b, which can be shifted radially in relation to part 33a, to be moved as well. A further worm gear arrangement 59 facilitates the radial shifting of part 33b relative to part 33a. The worm gear arrangement 59 also comprises a gear wheel 61, a worm wheel 63 and a crank disk 65 and exhibits the same advantages previously described.

Although various minor modifications may be suggested by those versed in the art, it should be understood that we wish to embody within the scope of the patent granted hereon all such modifications as reasonably and properly come within the scope of our contribution to the art.

We claim:

1. A holding mechanism for a measuring cryostat used for acquisition of biomagnetic signals, said mechanism comprising two vertically standing columns, each of said columns having a travelling box telescopically received thereon and displaceable therealong, a shackle extending between the two boxes having means at each end for forming a rotatable connection with the boxes, said shackle having means for mounting a cryostat, said means for mounting enabling pivoting of the cryostat in a shackle plane so that an axis of the cryostat can be rotated around a horizontal axis and pivoted relative to a vertical axis, a cross member connecting an upper end of each of the two vertically standing columns together, and each of the columns being hollow and receiving a counter-weight, said cross member forming a bridge for receiving cables connected to the counter-weights in each of the columns, said cables extending to the means for mounting the cryostat on the shackle so that movement of the shackle and boxes along the columns is counter-balanced by the weights in said columns.

2. A holding mechanism according to claim 1, wherein each of the means for mounting the shackle to the travelling boxes include a circular disk segment, which is rotatably mounted on a pin secured to the travelling box.

3. A holding mechanism according to claim 2, wherein one of the circular disk segments is provided with a gear rim on its circumference, said gear rim being engaged by a drive gear to control rotation of the shackle on the axis formed by said pins.

4. A holding mechanism according to claim 1, wherein the means for mounting the measuring cryostat includes a circular ring segment secured to a middle of the shackle, said ring segment having at least one circular-shaped channel, said means for mounting the cryostat being pivotably connected in said channel, and said ring segment being aligned to extend parallel to a shackle plane.

5. A holding mechanism according to claim 4, wherein the means for mounting the measuring cryostat includes means for adjusting the cryostat in a radial direction on the circular segment.

6. A holding mechanism according to claim 5, wherein the means for mounting the measuring cryostat includes means for enabling rotation of the cryostat around a central axis.

7. A holding mechanism according to claim 6, wherein the circular ring segment is provided with a detent to limit the amount of pivoting of the means for mounting the cryostat on the circular ring segment.

8. A holding mechanism according to claim 6, wherein the means for rotatably mounting the shackle to each of the travelling boxes includes a circular disk segment rotatable on a pin secured to the box.

9. A holding mechanism according to claim 2, wherein a worm gear arrangement is disposed between the circular disk segment and the travelling box.

10. A holding mechanism according to claim 4, wherein a worm gear arrangement for pivoting the cryostat is disposed between the circular ring segment and the cryostat.

11. A holding mechanism according to claim 5, wherein or gear arrangement for radially displacing the cryostat is disposed between the circular ring segment and the cryostat.

12. A holding mechanism according to claim 1, wherein the cross member has means for guiding the cables to a center of the cross member and then to a ring attached to said means for mounting the cryostat.

13. A holding mechanism according to claim 1, wherein the cross member is a hollow member with a cavity receiving deflection rollers for guiding said cables from the weights to said means for mounting the cryostat.

14. A holding mechanism according to claim 1, wherein said cross member has pulleys mounted therein, said cables extending from said weights over said pulleys to said means for mounting, said means for forming a rotatable connection including a disk rotatable on a pin secured to the box.

15. A holding mechanism according to claim 14, wherein the means for mounting the measuring cryostat on said shackle includes a circular ring segment having concentrically spaced circular channels, said means for mounting including tenon blocks received in each of said channels so that an axis of the cryostat can be pivoted around a given point as the shackle is rotated around the point.

16. A holding mechanism according to claim 15, wherein the circular ring segment has means to limit the amount of pivoting of the mounting means for the measuring cryostat in said channels to a given angle.

* * * * *